United States Patent [19]

Senn-Bilfinger

[11] Patent Number: 5,112,834

[45] Date of Patent: May 12, 1992

[54] IMIDAZOLE PROTECTORANT FOR THE STOMACH AND INTESTINE

[75] Inventor: Jörg Senn-Bilfinger, Konstanz, Fed. Rep. of Germany

[73] Assignee: BYK Gulden Lomberg Chemische Fabrik GmbH, Konstanz, Fed. Rep. of Germany

[21] Appl. No.: 445,611

[22] PCT Filed: Jul. 14, 1988

[86] PCT No.: PCT/EP88/00638

§ 371 Date: Jan. 16, 1990

§ 102(e) Date: Jan. 16, 1990

[87] PCT Pub. No.: WO89/00570

PCT Pub. Date: Jan. 26, 1989

[30] Foreign Application Priority Data

Jul. 16, 1987 [CH] Switzerland ............. 02709/87
Feb. 4, 1988 [CH] Switzerland ............. 00390/88

[51] Int. Cl.$^5$ .......... C07D 471/04; C07D 487/04; A61K 31/435; A61K 31/495
[52] U.S. Cl. .......... 514/300; 514/249; 544/350; 546/121
[58] Field of Search .......... 546/121; 514/300

[56] References Cited

U.S. PATENT DOCUMENTS

| | | | |
|---|---|---|---|
| 3,849,396 | 11/1974 | Birkenmeyer | 260/210 R |
| 3,849,576 | 11/1974 | Kalopissis | 424/330 |
| 3,852,279 | 12/1974 | Krapcho | 260/240 F |
| 4,324,796 | 4/1982 | Eistetter | 424/278 |
| 4,387,099 | 6/1983 | Smith | 424/263 |
| 4,387,219 | 6/1983 | Yamamoto | 536/13.6 |
| 4,395,414 | 7/1983 | Eistetter | 424/258 |
| 4,409,226 | 10/1983 | Bristol et al. | 546/121 |
| 4,430,339 | 2/1984 | Eistetter | 424/278 |
| 4,686,230 | 8/1987 | Rainer | 514/338 |
| 4,725,601 | 2/1988 | Ueda et al. | 544/350 |
| 4,758,579 | 7/1988 | Kohl | 514/338 |
| 4,831,041 | 5/1989 | Shiokawa et al. | 546/121 |
| 4,886,819 | 12/1989 | Ashimori | 514/356 |
| 4,920,129 | 4/1990 | Shiokawa et al. | 546/121 |

FOREIGN PATENT DOCUMENTS 33094 8/1981 European Pat. Off. .
204285 12/1986 European Pat. Off. .

Primary Examiner—Mukund J. Shah
Assistant Examiner—E. Beinhardt
Attorney, Agent, or Firm—Fleit, Jacobson, Cohn, Price, Holman & Stern

[57] ABSTRACT

Compounds of formula I,

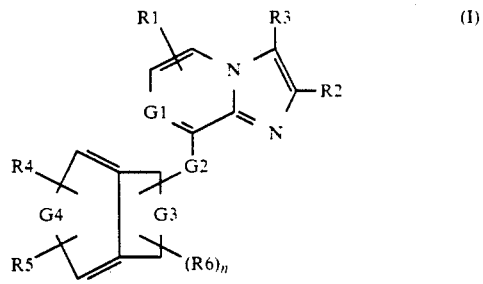

wherein the substituents and symbols having the meanings stated in the description are new compounds having interesting pharmacological properties. They have a protective effect on the stomach and intestine in warm-blooded animals.

11 Claims, No Drawings

IMIDAZOLE PROTECTORANT FOR THE STOMACH AND INTESTINE

FIELD OF USE OF THE INVENTION

The invention relates to new diazoles, processes for their preparation, their use and drugs containing them. The compounds according to the invention are used in the pharmaceutical industry as intermediates and for the manufacture of drugs.

KNOWN TECHNICAL BACKGROUND

The published European Patent Applications 0033094, 0068378, 0165545 and 0204285 disclose imidazopyridines and imidazoisoquinolines which, on account of their antisecretory and cytoprotective action, are intended for use in the treatment of ulcer.

DESCRIPTION OF THE INVENTION

It has been found that the new imidazole compounds described in greater detail below have interesting pharmacological properties, as a result of which they differ in a surprising and particularly advantageous manner from the above-mentioned known compounds.

The invention relates to new imidazole compounds of the formula I

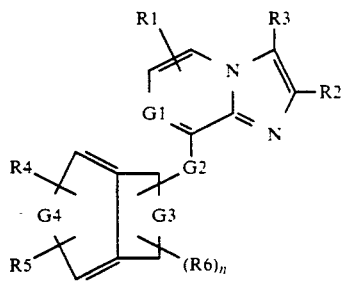

wherein

R1 denotes hydrogen (H) or halogen,

R2 denotes hydrogen (H), 1-4C-alkyl, hydroxy-1-4C-alkyl, halo-1-4C-alkyl, cyano-1-4C-alkyl or 1-4C-alkoxycarbonyl, R3 denotes hydrogen (H), 1-4C-alkyl, formyl, hydroxy-1-4C-alkyl, halo-1-4C-alkyl, cyano-1-4C-alkyl, amino-1-4C-alkyl, mono- or di-1-4C-alkylamino-1-4C-alkyl, nitroso, nitro, amino, mono- or di-1-4C-alkylamino or 1-4C-alkoxycarbonyl, R4 denotes hydrogen (H), 1-4C-alkyl, 1-4C-alkoxy, halogen or trifluoromethyl, R5 denotes hydrogen (H), 1-4C-alkyl, 1-4C-alkoxy, halogen or trifluoromethyl, R6 denotes hydrogen or 1-4C-alkyl, n denotes the numbers 1 or 2, G1 denotes CH or N (nitrogen), G2 denotes O (oxygen), NH, N-1-4C-alkyl or 1-4C-alkylene, G3 denotes 1-hydroxy-trimethylene (—CH(OH)—CH$_2$—CH$_2$—), 2-hydroxy-3-methyl-trimethylene (—CH$_2$—CH(OH)—CH(CH$_3$)—), 2-hydroxy-trimethylene (—CH$_2$—CH(OH)—CH$_2$—), 1-hydroxy-tetramethylene (—CH(OH)—CH$_2$—CH$_2$—CH$_2$—), 2-hydroxy-tetramethylene (—CH$_2$CH(OH)—CH$_2$—CH$_2$—), 1-hydroxy-pentamethylene (—CH(OH)—CH$_2$—CH$_2$—CH$_2$—CH$_2$—) or 2-hydroxy-pentamethylene (—CH$_2$—CH(OH)—CH$_2$—CH$_2$—CH$_2$—) and G4 denotes S (sulphur), O (oxygen) or vinylene (—CH=CH—), and their salts.

For the purposes of the present invention, halogen is bromine and in particular chlorine and fluorine.

1-4C-alkyl represents straight-chain or branched alkyl radicals having 1 to 4 carbon atoms. The butyl, isobutyl, secbutyl, tert-butyl, propyl, isopropyl, ethyl radicals and in particular the methyl radical may be mentioned as examples.

1-4C-alkoxy radicals contain, in addition to the oxygen atom, one of the above-mentioned 1-4C-alkyl radicals. The methoxy radical is preferred.

1-4C-alkoxycarbonyl radicals contain, in addition to the carbonyloxy group, one of the above-mentioned 1-4C-alkyl radicals. The methoxycarbonyl and the ethoxycarbonyl radicals are preferred.

Hydroxy-1-4C-alkyl represents the above-mentioned 1-4C-alkyl radicals to which a hydroxyl radical is bonded. The hydroxymethyl radical is preferred.

Halo-1-4C-alkyl represents the above-mentioned 1-4C-alkyl radicals to which a halogen atom is bonded. The chloromethyl radical is preferred.

Cyano-1-4C-alkyl represents the above-mentioned 1-4C-alkyl radicals to which a cyano radical is bonded. The cyanomethyl radical is preferred.

Amino-1-4C-alkyl represents the above-mentioned 1-4C-alkyl radicals to which an amino group is bonded.

Mono- or di-1-4C-alkylamino represents amino groups which are substituted by one or two of the above-mentioned 1-4C-alkyl radicals. The methylamino, ethylamino, diisopropylamino and in particular the dimethylamino groups may be mentioned as examples.

Mono- or di-1-4C-alkylamino-1-4C-alkyl represents the above-mentioned 1-4C-alkyl radicals to which one of the above-mentioned mono- or di-1-4C-alkylamino groups is bonded. The dimethylaminomethyl and the dimethylaminoethyl radicals are preferred.

1-4C-alkylene represents straight-chain alkylene radicals having 1 to 4 carbon atoms. The ethylene radical (—CH$_2$—CH$_2$—) and the methylene radical (—CH$_2$—) may be mentioned as preferred alkylene radicals.

Preferred salts for compounds of the formula I are all acid addition salts. The pharmacologically tolerated salts of the inorganic and organic acids usually used in the pharmaceutical sector may be mentioned in particular. Pharmacologically non-tolerated salts, which, for example, may initially be obtained as products of the process in the preparation of the compounds according to the invention on an industrial scale are converted into pharmacologically tolerated salts by processes known to one skilled in the art. Suitable salts of this type are, for example, water soluble and water-insoluble acid addition salts, such as hydrochloride, hydrobromide, hydroiodide, phosphate, nitrate, sulphate, acetate, citrate, gluconate, benzoate, hibenzate, fendizoate, butyrate, sulphosalicylate, maleate, laurate, malate, fumarate succinate, oxalate, tartrate, amsonate, embonate, metemborate, stearate, tosylate, 2-hydroxy-3-naphthoate, 3-hydroxy-2-naphthoate or mesylate.

On the other hand, however, quaternary ammonium salts, which can be obtained by reacting compounds of the formula I with suitable alkylating agents, are also suitable salts. 1-4C-alkyl halides, preferably methyl iodide, or benzyl halides, such as benzyl bromide, or allyl halides such as allyl bromides, may be mentioned as suitable alkylating agents.

Furthermore all alcoholates shall be mentioned as suitable salts, which are obtained by reacting compounds of formula I with appropriate deprotonation agents (e.g. strong bases). Organometallic compounds, such as butyl lithium, or alkali hydrides, such as sodium hydride, may be mentioned as suitable deprotonation agents.

The invention relates in particular to compounds of formula I in which the G2 group is linked to a carbon atom of the G3 alkylene group, which is directly adjacent to a hydroxyl substituted carbon atom. The compounds according to the invention have at least two assymetric carbon atoms in group G3. The invention encompasses all conceivable combinations, i.e. the R,R-, R,S-, S,R- and S,S-combinations. The invention relates preferentially to the optically pure compounds of formula I.

Noteworthy compounds according to the invention are those of formula I, wherein
R1 denotes hydrogen, chlorine or fluorine,
R2 denotes hydrogen, methyl, ethyl, hydroxymethyl, chloromethyl, cyanomethyl, methoxycarbonyl or ethoxycarbonyl,
R3 denotes hydrogen, methyl, formyl, hydroxymethyl, chloromethyl, cyanomethyl, dimethylaminomethyl, amino, dimethylamino, methoxycarbonyl or ethoxycarbonyl,
R4 denotes hydrogen, methyl, methoxy, chlorine, fluorine or trifluoromethyl,
R5 denotes hydrogen, methyl, methoxy, chlorine or fluorine,
R6 denotes hydrogen or methyl.
n denotes numbers 1 or 2
G1 denotes CH or N (nitrogen),
G2 denotes O (oxygen), NH or methylene,
G3 1-hydroxy-trimethylene (—CH(OH)—CH$_2$—CH$_2$—), 2-hydroxy-3-methyl-trimethylene (—CH$_2$—CH(OH)—CH(CH$_3$)—, 2-hydroxy-trimethylene (—CH$_2$—CH(OH)—CH$_2$—), 1-hydroxy-tetramethylene (—CH(OH)—CH$_2$—CH$_2$—CH$_2$—), 2-hydroxy-tetramethylene (—CH$_2$—CH(OH )—CH$_2$—CH$_2$—), 1-hydroxy-pentamethylene (—CH(OH)—CH$_2$—CH$_2$—CH$_2$—CH$_2$—) or 2-hydroxy-pentamethylene (—CH$_2$—CH—(OH)—CH$_2$—CH$_2$—CH$_2$—) and
G4 denotes O (oxygen), S (sulphur) or vinylene (—CH=CH—), and their salts.

Compounds according to the invention which may be singled out are those of formula I*,

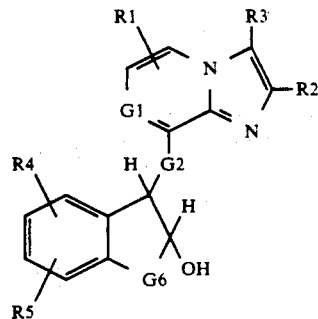

(I*)

wherein
R1 denotes hydrogen, chlorine or fluorine,
R2 denotes hydrogen, methyl, ethyl or hydroxymethyl,
R3 denotes hydrogen, methyl formyl, hydroxymethyl, cyanomethyl or amino,
R4 denotes hydrogen, methyl, ethyl, methoxy, ethoxy, chlorine, fluorine or trifluoromethyl,
R5 denotes hydrogen, methyl, ethyl, chlorine or fluorine,
G1 denotes CH
G2 denotes O (oxygen) or NH and
G6 denotes —CH$_2$—, —CH(CH$_3$)—, —CH$_2$CH$_2$— or —CH$_2$CH$_2$CH$_2$—, and their salts.

Compounds according to the invention which may be singled out as examples are those of formula I*, wherein
R1 denotes hydrogen or halogen,
R2 denotes 1-4C-alkyl,
R3 denotes hydrogen, 1-4C-alkyl, formyl, hydroxymethyl, cyanomethyl or amino,
R4 denotes hydrogen or halogen,
R5 denotes hydrogen,
G1 denotes CH,
G2 denotes O (oxygen) or NH,
G6 denotes —CH$_2$—, —CH$_2$CH$_2$— or —CH$_2$CH$_2$CH$_2$—, and their salts.

Preferred compounds according to the invention are those of formula I*, wherein
R1 denotes hydrogen,
R2 denotes methyl
R3 denotes hydrogen, methyl, hydroxymethyl, cyanomethyl or amino,
R4 denotes hydrogen or fluorine,
R5 denotes hydrogen,
G1 denotes CH,
G2 denotes O (oxygen) or NH and
G6 denotes —CH$_2$— or —CH$_2$CH$_2$— and their salts.

Selected compounds according to the invention may be characterised by the following formulae Ia and Ib,

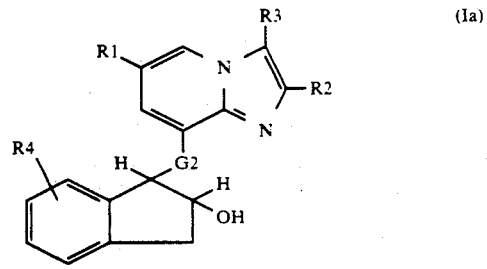

(Ia)

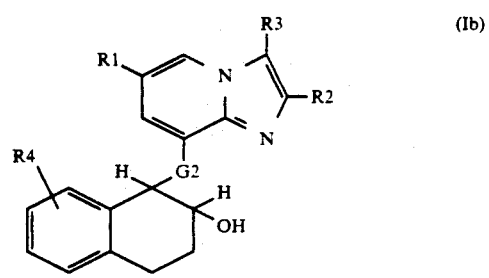

(Ib)

wherein the substituents and symbols R1, R2, R3, R4 and G2 have the above-stated meanings. Taking the absolute configuration at positions 1' and 2' in the dihydroindenyl and tetrahydronaphthyl radicals into account, the selected compounds give rise to the following particularly preferred optically pure configuration isomers,

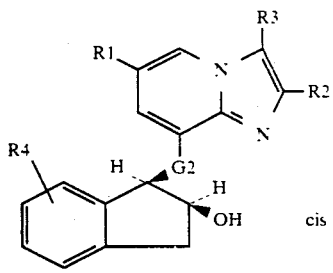 (Ia')

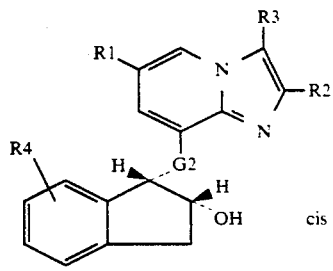 (Ia")

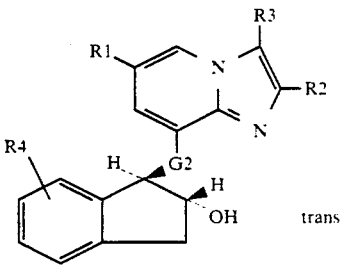 (Ia'")

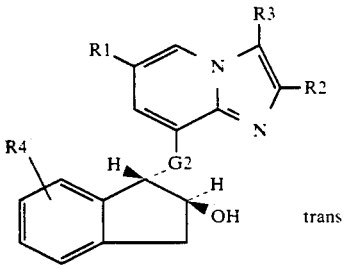 (Ia"")

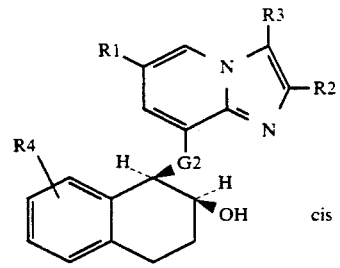 (Ib')

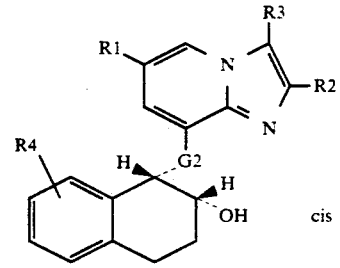 (Ib")

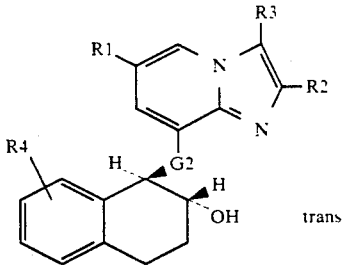 (Ib'")

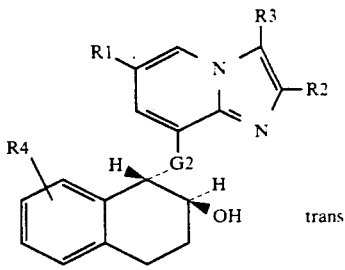 (Ib"")

wherein R1, R2, R3, R4 and G2 have the above-stated meanings.

The following may be mentioned as examples of the compounds according to the invention to be singled out in particular:

8(2hydroxy-1,2,3,4-tetrahydro-1-naphthyloxy)-2-methyl-imidazo[1,2-a]pyridine 8-(2-hydroxy-1,2,3,4-tetrahydro-1-naphthyloxy)-2,3-dimethyl-imidazo[1,2-a]pyridine 8-(2-hydroxy-1,2,3,4-tetrahydro-1-naphthyloxy)-3-hydroxymethyl-2-methyl-imidazo[1,2-a]pyridine 3-cyanomethyl-8-(2-hydroxy-1,2,3,4-tetrahydro-1-naphthyloxy)-2-methyl-imidazo[1,2-a]pyridine 8-(2-hydroxy-1,2,3,4-tetrahydro-1-naphthyloxy)-2-hydroxymethyl-3-methyl-imidazo[1,2-a]pyridine 8-(2-hydroxy-1,2,3,4-tetrahydro-1-naphthylamino)-2-methyl-imidazo[1,2-a]pyridine 8-(2-hydroxy-1,2,3,4-tetrahydro-1-naphthylamino)-2,3-dimethyl-imidazo[1,2-a]pyridine 3-hydroxymethyl-8-(2-hydroxy-1,2,3,4-tetrahydro-1-naphthylamino)-2-methyl-imidazo[1,2-a]pyridine 3-cyanomethyl-8-(2-hydroxy-1,2,3,4-tetrahydro-1-naphthylamino)-2-methyl-imidazo[1,2-a]pyridine 2-hydroxymethyl-8-(2-hydroxy-1,2,3,4-tetrahydro-1-naphthylamino-3-methyl-imidazo[1,2-a]pyridine 3-amino-8-(2-hydroxy-1,2,3,4-tetrahydro-1-naphthyloxy)-2-methyl-imidazo[1,2-a]-pyridine 3-amino-8-(2-hydroxy-2,3-dihydro-1-indenyloxy)-2-methyl-imidazo[1,2-a]pyridine 8-(2-hydroxy-2,3-dihydro-1-indenyloxy)-2-methyl-imidazo-[1,2-a]pyridine 8-(2-hydroxy-2,3-dihydro-1-indenyloxy)-2,3-dimethyl-imidazo-[1,2a-]pyridine 3-hydroxymethyl-8-(2-hydroxy-2,3-dihydro-1-indenyloxy)-2-methyl-imidazo[1,2-a]pyridine 2-ethyl-3-hydroxymethyl-8-(2-hydroxy-2,3-dihydro-1-indenyloxy)-imidazo-[1,2-a]pyridine 3-cyanomethyl-8-(2-hydroxy-2,3-dihydro-1-indenyloxy)-2-methyl-imidazo[1,2-a]pyridine 2-hydroxymethyl-8-(2-hydroxy-2,3-dihydro-1-indenyloxy)-3-methyl-imidazo[1,2-a]pyridine 3-amino-8-(2-hydroxy-2,3-dihydro-1-indenylamino)-2-methyl-imidazo[1,2-a]pyridine 8-(2-hydroxy-2,3-dihydro-1-indenylamino)-2-methyl-imidazo[1,2-a]-pyridine
8-(2-hydroxy-2,3-dihydro-1-indenylamino)-2,3-dimethyl-imidazo[1,2-a]pyridine
3-hydroxymethyl-8-(2-hydroxy-2,3-dihydro-1-indenylamino)-2-methyl-imidazo[1,2-a]pyridine
3-cyanomethyl-8-(2-hydroxy-2,3-dihydro-1-indenylamino)-2-methyl-imidazo[1,2-a]pyridine
2-hydroxymethyl-8-(2-hydroxy-2,3-dihydro-1-indenylamino)-3-methyl-imidazo[1,2-a]pyridine
3-amino-8-(6-fluoro-2-hydroxy-1,2,3,4-tetrahydro-1-naphthyloxy)-2-methyl-imidazo[1,2-a]pyridine
8-(6-fluoro-2-hydroxy-1,2,3,4-tetrahydro-1-naphthyloxy)-2-methyl-imidazo[1,2-a]pyridine
8-(6-fluoro-2-hydroxy-1,2,3,4-tetrahydro-1-naphthyloxy)-2,3-dimethyl-imidazo[1,2-a]pyridine
8-(6-fluoro-2-hydroxy-1,2,3,4-tetrahydro-1-naphthyloxy)-3-hydroxymethyl-2-methyl-imidazo[1,2-a]pyridine
3-cyanomethyl-8-(6-fluoro-2-hydroxy-1,2,3,4-tetrahydro-1-naphthyloxy)-2-methyl-imidazo[1,2-a]pyridine
8-(6-fluoro-2-hydroxy-1,2,3,4-tetrahydro-1-naphthyloxy)-2-hydroxymethyl-3-methyl-]imidazo[1,2-a]pyridine
8-(6-fluoro-2-hydroxy-1,2,3,4-tetrahydro-1-naphthylamino)-2-methyl-imidazo[1,2-a]pyridine
8-(6-fluoro-2-hydroxy-1,2,3,4-tetrahydro-1-naphthylamino)-2,3-dimethyl-imidazo[1,2-a]pyridine
8-(6-fluoro-2-hydroxy-1,2,3,4-tetrahydro-1-naphthylamino)-3-hydroxymethyl-2-methyl-imidazo [1,2-a]pyridine
3-cyanomethyl-8-(6-fluoro-2-hydroxy-1,2,3,4-tetrahydro-1-naphthylamino)-2-methyl-imidazo[1,2-a]pyridine
8-(6-fluoro-2-hydroxy-1,2,3,4-tetrahydro-1-naphthylamino)-2-hydroxymethyl-3-methyl-imidazo[1,2-a]pyridine
8-(5-fluoro-2-hydroxy-2,3-dihydro-1-indenyloxy)-2-methyl-imidazo[1,2-a]pyridine
3-amino-8-(5-fluoro-2-hydroxy-2,3-dihydro-1-indenyloxy)-2-methyl-imidazo[1,2-a]pyridine
8-(5-fluoro-2-hydroxy-2,3-dihydro-1-indenyloxy)-2,3-dimethyl-imidazo[1,2-a]pyridine
8-(5-fluoro-2-hydroxy-2,3-dihydro-1-indenyloxy)-3-hydroxy-methyl-2-methyl-imidazo[1,2-a]pyridine
2-ethyl-8-(5-fluoro-2-hydroxy-2,3-dihydro-1-indenyloxy)-3-hydroxymethyl-imidazo[1,2-a]pyridine
3-cyanomethyl-8-(5-fluoro-2-hydroxy-2,3-dihydro-1-indenyloxy)-2-methyl-imidazo[1,2-a]pyridine
8-(5-fluoro-2-hydroxy-2,3-dihydro-1-indenyloxy)-2-hydroxy-methyl-3-methyl-imidazo[1,2-a]pyridine
8-(5-fluoro-2-hydroxy-2,3-dihydro-1-indenylamino)-2-methyl-imidazo[1,2-a]pyridine
8-(5-fluoro-2-hydroxy-2,3-dihydro-1-indenylamino)-2,3-dimethyl-imidazo[1,2-a]pyridine
8-(5-fluoro-2-hydroxy-2,3-dihydro-1-indenylamino)-3-hydroxy-methyl-2-methyl-imidazo[1,2-a]pyridine
3-cyanomethyl-8-(5-fluoro-2-hydroxy-2,3-dihydro-1-indenylamino)-2-methyl-imidazo[1,2-a]pyridine
8-(5-fluoro-2-hydroxy-2,3-dihydro-1-indenylamino)-2-hydroxymethyl-3-methyl-imidazo[1,2-a]pyridine
3-amino-8-(2-hydroxy-3-methyl-2,3-dihydro-1-indenyloxy)-2-methyl-imidazo[1,2-a]pyridine
8-(2-hydroxy-3-methyl-2,3-dihydro-1-indenyloxy)-2-methyl-imidazo[1,2-a]pyridine
8-(2-hydroxy-3-methyl-2,3-dihydro-1-indenyloxy)-2,3-dimethyl-imidazo[1,2-a]pyridine
3-hydroxymethyl-8-(2-hydroxy-3-methyl-2,3-dihydro-1-indenyloxy)-2-methyl-imidazo[1,2-a]pyridine
2-ethyl-3-hydroxymethyl-8-(2-hydroxy-3-methyl-2,3-dihydro-1-indenyloxy)-imidazo[1,2-a]pyridine
3-cyanomethyl-8-(2-hydroxy-3-methyl-2,3-dihydro-1-indenyloxy)-2-methyl-imidazo[1,2-a]pyridine
2-hydroxymethyl-8-(2-hydroxy-3-methyl-2,3-dihydro-1-indenyloxy)-3-methyl-imidazo[1,2-a]pyridine
8-(2-hydroxy-3-methyl-2,3-dihydro-1-indenylamino)-2-methyl-imidazo[1,2-a]pyridine
8-(2-hydroxy-3-methyl-2,3-dihydro-1-indenylamino)-2,3-dimethyl-imidazo[1,2-a]pyridine
3-hydroxymethyl-8-(2-hydroxy-3-methyl-2,3-dihydro-1-indenylamino)-2-methyl-imidazo[1,2-a]pyridine
3-cyanomethyl-8-(2-hydroxy-3-methyl-2,3-dihydro-1-indenylamino)-2-methyl-imidazo[1,2-a]pyridine
2-hydroxymethyl-8-(2-hydroxy-3-methyl-2,3-dihydro-1-indenylamino)-3-methyl-imidazo[1,2-a]pyridine
3-amino-8-(5-chloro-2-hydroxy-2,3-dihydro-1-indenyloxy)-2-methyl-imidazo[1,2-a]-pyridine
3-amino-8-(5,6-dichloro-2-hydroxy-2,3-dihydro-1-indenyloxy)-2-methyl-imidazo[1,2-a]pyridine
3-amino-8-(5,6-difluoro-2-hydroxy-2,3-dihydro-1-indenyloxy)-2-methyl-imidazo[1,2-a]pyridine
3-amino-8-(5,6-difluoro-2-hydroxy-2,3-dihydro-3-methyl-1-indenyloxy)-2-methyl-imidazo[1,2-a]pyridine
3-amino-8-(5-fluoro-2-hydroxy-2,3-dihydro-3-methyl-1-indenyloxy)-2-methyl-imidazo[1,2-a]pyridine
3-amino-8-(4-fluoro-2-hydroxy-2,3-dihydro-1-indenyloxy)-2-methyl-imidazo[1,2-a]pyridine
3-amino-8-(6-fluoro-2-hydroxy-2,3-dihydro-1-indenyloxy)-2-methyl-imidazo[1,2-a]pyridine
3-amino-8-(4-chloro-2-hydroxy-2,3-dihydro-1-indenyloxy)-2-methyl-imidazo[1,2-a]pyridine
3-amino-8-(6-chloro-2-hydroxy-2,3-dihydro1-indenyloxy)-2-methyl-imidazo[1,2-a]pyridine
3-amino-8-(7-chloro-2-hydroxy-2,3-dihydro-1-indenyloxy)-2-methyl-imidazo[1,2-a]pyridine
8-(5-chloro-2-hydroxy-2,3-dihydro-1-indenyloxy)-3-hydroxymethyl-2-methyl-imidazo[1,2-a]pyridine
8-(5,6-dichloro-2-hydroxy-2,3-dihydro-1-indenyloxy)-3-hydroxymethyl-2-methyl-imidazo[1,2-a]pyridine
8-(5,6-difluoro-2-hydroxy-2,3-dihydro 1-indenyloxy)-3-hydroxymethyl-2-methyl-imidazo[1,2-a]pyridine
8-(5,6-difluoro-2-hydroxy-2,3-dihydro 3-methyl-1-indenyloxy)-3-hydroxymethyl-2-methyl-imidazo[1,2-a]pyridine
8-(5-fluoro-2-hydroxy-2,3-dihydro-3-methyl-1-indenyloxy)-3-hydroxymethyl-2-methyl-imidazo[1,2-a]pyridine
8-(4-fluoro-2-hydroxy-2,3-dihydro-1-indenyloxy)-3-hydroxymethyl-2-methyl-imidazo[1,2-a]pyridine
8-(6-fluoro-2-hydroxy-2,3-dihydro-1-indenyloxy)-3-hydroxymethyl-2-methyl-imidazo[1,2-a]pyridine
8-(4-chloro-2-hydroxy-2,3-dihydro-1-indenyloxy)-3-hydroxymethyl-2-methyl-imidazo[1,2-a]pyridine
8-(6-chloro-2-hydroxy-2,3-dihydro-1-indenyloxy)-3-hydroxymethyl-2-methyl-imidazo[1,2-a]pyridine
8-(7-chloro-2-hydroxy-2,3-dihydro-1-indenyloxy)-3-hydroxymethyl-2-methyl-imidazo[1,2-a]pyridine
and the salts of these compounds.

The optically pure forms (1R,2R), (1R,2S), (1S,2R) and (1S,2S) of the above-mentioned compounds and their salts are preferred.

The invention furthermore relates to a process for the preparation of the compounds according to the invention and their salts. The process is characterised by the fact that imidazopyridines of formula II are reacted with bicycles of formula III

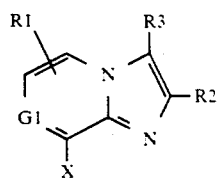 (II)

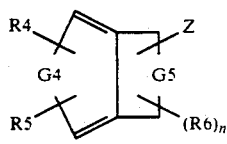 (III)

and, if desired, the compounds obtained of formula I, wherein R3 means formyl or nitroso, are reduced to the compounds of formula I, wherein R3 means hydroxymethyl or amino, and/or if desired salts obtained are converted into free compounds or the free compounds obtained are converted into the salts wherein the original compounds are used as such or in the form of their salts and wherein R1, R2, R3, R4, R5, R6, n, G1 and G4 denote the above-stated meanings, G5 together with the Z represents a group which can react with X to form the groups G2 and G3, or G5 denotes G3 and X and Z represent suitable reactive groups which can react to form group G2.

The type of reaction of the imidazopyridine II compounds with the bicycle III compounds depends on the structures of the reactive groups G5, X and Z, which in turn are dependent on the desired groups G2. The following reactive groups are mentioned as examples of dependence on G2:

| | | |
|---|---|---|
| G2 = O (oxygen) | X = OH | Z = halogen |
| | or X = OH | G5 = G3 |
| | | G5 and Z together represent a 1,2-epoxy-trimethylene, 1,2- or 2,3-epoxytetramethylene or 1,2 or 2,3-epoxypentamethylene group. |
| G2 = NH | X = NH$_2$ | Z = halogen |
| | or X = NH$_2$ | G5 = G3 |
| | | G5 and Z together represent a 1,2-epoxy-trimethylene, 1,2- or 2,3-epoxytetramethylene or 1,2 or 2,3-epoxypentamethylene group. |
| G2 = N-1-4C-alkyl | X = NH-1-4C-alkyl | Z = halogen |
| | or X = NH-1-4C-alkyl | G5 = G3 |
| | | G5 and Z together represent a 1,2-epoxy-trimethylene, 1,2- or 2,3-epoxytetramethylene or 1,2 or 2,3-epoxypentamethylene group. |
| G2 = 1-4C-alkylene | X = alkali metal-1-4C-alkyl | Z = halogen |
| | or X = alkali metal-1-4C-alkyl | G5 = G3 |
| | | G5 and Z together represent a 1,2-epoxy-trimethylene, 1,2- or 2,3-epoxytetramethylene or 1,2 or 2,3-epoxypenta-methylene group. |

The reaction of II with III is carried out in suitable, inert solvents, in which reaction condensation with cleavage of H-halogen requires the presence of : suitable base or previous deprotonation (e.g. with a hydride, such as sodium hydride). If the epoxides rather than the halogen alcohols of the bicycle compounds III are used, the reaction with the imidazopyridine compounds II takes place in the presence of aluminium oxide or preferentially in polar, proton-containing media in the presence of bases. The proton-containing media are water and alcohols, preferentially methanol, alone or in combination. The bases are alkali or alkaline earth hydroxides, preferentially alkali carbonates and tertiary organic amines. Depending on the type they may be used in excess or in insufficient amounts, 0.1-2 mol. being preferred. Reaction in polar media is carried out at temperatures ranging from 0° to 100° C., the range of 20° to 60° C. being preferred.

Preparation of epoxides from suitable precursors, e.g. halogen alcohols, can also take place in situ and be combined in the one-pot procedure with their reaction with compounds II, using at least one further mol of base. The preferred preparation of compounds according to the invention takes place by reaction of the imidazopyridine compounds II (with X=OH or NH$_2$) with 1,2-epoxides, giving rise almost exclusively to the trans-addition product.

The reduction of compounds I, wherein R3 denotes formyl, to compounds I, wherein R3 denotes hydroxymethyl, takes place in a manner used by one skilled in the art, e.g. by reaction of the formyl compound with sodium borohydride.

The reduction of compounds I, wherein R3 denotes nitroso, to compounds I, wherein R3 denotes amino, takes place in a manner used by one skilled in the art, e.g. by reaction of the nitroso compound with zinc powder in acidic medium.

These specific reaction conditions required for carrying out the process are familiar to one skilled in the art from his technical knowledge.

The substances according to the invention are isolated and purified in a manner known per se, for example by distilling off the solvent in vacuo and recrystallizing the resulting residue from a suitable solvent or subjecting it to one of the usual purification methods such as, for example, column chromatography over suitable carrier material.

Acid addition salts are obtained by dissolving the free base in a suitable solvent, for example in a chlorinated hydrocarbon, such as methylene chloride or chloroform, or in a low molecular weight aliphatic alcohol (ethanol or isopropanol) which contains the desired acid or to which the desired acid is subsequently added.

The salts are obtained by filtration, reprecipitation, precipitation with a nonsolvent for the addition salt or evaporation of the solvent. Salts obtained can be converted by alkalization, for example with aqueous ammonia solution, into the free bases, which in turn can be converted into acid addition salts. Pharmacologically non-tolerated acid addition salts can be converted into pharmacologically tolerated acid addition salts in this manner.

Quarternary ammonium salts are obtained in an analogous manner by dissolving the free base in a suitable solvent, for example in acetone, or in a chlorinated hydrocarbon, such as methylene chloride or chloroform, to which the desired alkylating agent is subsequently added. These salts too are obtained by filtration, reprecipitation, precipitation with a nonsolvent for the addition salt or evaporation of the solvent.

Alcoholates are obtained for example by reaction of the compounds according to the invention with alkali metals or alkali metal hydrides.

Enantiomeric pure compounds I are obtained for example by reaction of enantiomeric pure bicycle compounds III with the imidazopyridine compounds II. The enantiomeric pure compounds I with the trans-configuration (such as Ia''', Ia'''', Ib''' and Ib'''') are obtained as trans-addition products preferably by reaction of the corresponding enantiomeric pure epoxides with the imidazopyridine compounds II. The enantiomeric pure compounds I with a cis-configuration (such as Ia', Ia''', Ib' and Ib'') are for example obtained by a epimerization of the trans-configuration isomers. Epimerization is carried out for example—starting with the corresponding mesylate—by reaction with potassium acetate in the presence of a crown ether and subsequent saponification.

The starting compounds II are known from the literature or can be prepared analogously to methods known from the literature, for example analogously to J. J. Kaminski et al. [J. Med. Chem. 28, 876 (1985)] or as described in the European Patent Applications 33 094 or 68 378. The starting compounds III are also known from the literature [see for example G. H. Posner et al., J. Amer. Chem. Soc. 99, 8214 (1977), M. N. Akhtar et al., J. Chem. Soc. Perk. Trans. I (1979) 2437; D. R. Boyd et al., J. Chem. Soc. Perk. Trans. I (1982) 2767 and Bull. Soc. Chim. (France) 11, 3092–3095 (1973)] or they can also be produced analogously to methods known from the literature.

Preferred embodiments of the process are those, wherein the substituents and symbols R1, R2, R3, R4, R5, R6, n, G1, G2, G3, G4 and G6 have the meanings given in the alternative independent claims and in the dependent claims.

The following Examples illustrate the invention in more detail without restricting it. The compounds of the general formula I which are mentioned by name in the Examples and the salts of these compounds are preferred subjects of the invention. Mp. denotes melting point, and the abbreviation h is used for hour(s) and the abbreviation min. is used for minutes. "Ether" is understood as diethyl ether.

EXAMPLES

End Products

1.

8-(2-(trans)-hydroxy-2,3-dihydro-1-indenylamino)-2-methyl-imidazo[1,2-a]-pyridine 7.5 g aluminium oxide (Woelm 200) is added to a suspension of 1 mMol 8-amino-2-methyl-imidazo[1,2a]-pyridine in dry diethyl ether. This is stirred for 30 minutes at room temperature and 1 mMol 1,2-indenoxide is added. The heterogeneous mixture is stirred for 2 to 48 hours at room temperature. It is then filtered off and the filtrate freed of solvent. The filter cake is mixed with 3×50 ml methanol, the aluminium oxide filtered off and the filtrate is dried in a vacuum. The original filtrate is combined with the filtrate of the methanol mixture, dried and subsequently purified over silica gel (mobile phase: methylene chloride/methanol=95:5). After recrystallization from acetonitrile, the title compound is obtained at m.p. 188°–190° C.

2.

8-2-(trans)-hydroxy-2,3-dihydro-1-indenyloxy)-2,3-dimethyl-imidazo[1,2-a]pyridine The title compound of m.p. 182°–183° C. is obtained by reaction of 2,3-dimethyl-8-hydroxy-imidazo[1,2-a]pyridine with 1,2- indenoxide analogously to the method described in Example 1 and after recrystallization from diethyl ether.

3.

8-(2-(trans)-hydroxy-2,3-dihydro-1-indenyloxy)-2-methyl-imidazo[1,2-a]pyridine

The title compound of m.p. 156°–157° C. is obtained by reaction of 8-hydroxy-2-methyl-imidazo[1,2-a]pyridine with 1,2-indenoxide analagously to the method given in Example 1.

4.

3-cyanomethyl-8-(2-(trans)-hydroxy-2,3-dihydro-1-indenyloxy)-2-methyl-imidazo[1,2-a]pyridine The title compound of m.p. 181°–183° C. is obtained by reaction of 3-cyanomethyl-8-hydroxy-2-methyl-imidazo[1,2-a]pyridine with 1,2 indenoxide analogously to the method described in Example 1.

5.

8-(2-(trans)-hydroxy-1,2,3,4-tetrahydro-1-naphthyloxy)-2,3-dimethyl-imidazo[1,2-a]pyridine The title compound is obtained as a viscous oil by reaction of 2,3-dimethyl-8-hydroxy-imidazo[1,2-a]pyridine with 1,2,3,4-tetrahydronaphthaline-1,2-oxide analogously to the method described in Example 1.

6.

3-cyanomethyl-8-(2-(trans)-hydroxy-1,2,3,4-tetrahydro-1-naphthyloxy)-2-methyl-imidazo[1,2-a]pyridine The title compound of m.p. 154°–155° C. is obtained by reaction of 3-cyanomethyl-8-hydroxy-2-methyl-imididazo[1,2-a]pyridine with 1,2,3,4-tetrahydronaphthaline-1,2-oxid analogously to the method described in Example 1.

7.

3-formyl-8-(2-(trans)-hydroxy-2,3-dihydro-1-indenyloxy)-2-methyl-imidazo[1,2-a]pyridine The title compound of m.p. 200°–202° C. is obtained by reaction of 3-formyl-8-hydroxy-2-methyl-imidazo[1,2-a]pyridine with 1,2-indenoxide analogously to the method described in Example 1.

8.

3-hydroxymethyl-8-(2-(trans)-hydroxy-2,3-dihydro-1-indenyloxy)-2-methyl-imidazo[1,2-a]pyridine 1 g of 3-formyl-8-(2-(trans)-hydroxy-2,3-dihydro-1-indenyloxy)-2-methyl-imidazo[1,2-a]pyridine is dissolved in 150 ml methanol, and excess sodium boro hydride is added in small portions at room temperature. After reduction has been completed, 150 ml icewater is added. The volatile components are evaporated in the rotary evaporator in vacuo. Subsequently extraction is carried out 3×with 40 ml ethyl acetate each time. The combined extracts are stripped off in vacuo of solvents, and the crystalline residue is recrystallized from methanol. The title compound of 192°–193° C. is obtained.

9.
8-(2-(trans)-hydroxy-2,3-dihydro-1-indenyloxy)-2-methyl-3-nitroso-imidazo[1,2-a]pyridine 0.5 g 8-(2-(trans)-hydroxy-2,3-dihydro-1-indenyloxy)-2-methyl-imidazo[1,2-a]pyridine, dissolved in 50 ml tetrahydrofuran, are mixed with 0.6 g commercial butyl nitrite at 50° C. and left over night at this temperature. After evaporation of the volatile components in vacuo, residue is washed with few cold acetonitrile and, after the solvent is poured off, recrystallized from acetonitrile. 0.35 g yellow title compound of m.p. 178°–179° C. is obtained.

10.
3-amino-8-(2-(trans)-hydroxy-2,3-dihydro-1-indenyloxy)-2-methyl-imidazo[1,2-a]pyridine 0.5 g of 8-(2-(trans)-hydroxy-2,3-dihydro-1-indenyloxy)-2-methyl-3-nitroso-imidazo[1,2-a]pyridine is dissolved in a mixture consisting of 10 ml glacial acetic acid and 3 ml water and 0.5 g commercial zinc powder is added at 0° C. waterbath temperature. After one hour the solution is diluted with 100 ml icewater adjusted to pH 8 with saturated sodium hydrogen carbonate solution and extracted with ethyl acetate. The combined extracts are dried over potassium carbonate. After removal of the solvent in vacuo, the mixture is purified over silica gel (methylene chloride/methanol=98/02). After recrystallization from ethanol the title compound of 125°–127° C. is obtained.

11.
3-amino-8-(2-(trans)-hydroxy-2,3-dihydro-1-indenyloxy)-2-methyl-imidazo[1,2-a]pyridine-hydrochloride 0,8 g of 3-amino-8-(2-(trans)-hydroxy-2,3-dihydro-1-indenyloxy)-2-methyl-imidazo[1,2-a pyridine is heat dissolved in 25 ml isopropanol and mixed at 20° C. with excess saturated ethereal hydrochloric acid. The precipitating title compound is filtered off under suction. m.p. 145°–147° C.

12.
8-(2-(trans)-hydroxy-1,2,3,4-tetrahydro-1-naphthyloxy)-2-methyl-imidazo[1,2-a]pyridine The title compound of m.p. 196°–197° C. is obtained from 8-hydroxy-2-methyl-imidazo[1,2-a]pyridine by reaction with 1,2,3,4-tetrahydronaphthaline-1,2-oxide analogously to the method described in Example 1 and after recristallization from acetonitrile.

13.
3-formyl-8-(2-(trans)-hydroxy-1,2,3,4-tetrahydro-1-naphthyloxy)-2-methyl-imidazo[1,2-a]pyridine The title compound of m.p. 183°–184° C. is obtained from 3-formyl-8-hydroxy-2-methyl-imidazo[1,2-a]pyridine in reaction with 1,2,3,4-tetrahydronaphthaline-1,2-oxide analogously to the method described in Example 1 and after recrystallization from isopropanol.

14.
3-hydroxymethyl-8-(2-(trans)-hydroxy-1,2,3,4-tetrahydro-1-naphthyloxy)-2-methyl-imidazo[1,2-a]pyridine Analogously to Example 8, the title compound of m.p. 106°–108° C. is obtained by reduction of 3-formyl-8-(2-(trans)-hydroxy-1,2,3,4-tetrahydro-1-naphthyloxy)-2-methyl-imidazo[1,2-a]pyridine with sodium borohydride.

15.
8-(2-(trans)-hydroxy-1,2,3,4-tetrahydro-1-naphthyloxy)-2-methyl-3-nitroso-imidazo[1,2-a]pyridine Nitrosation of 8-(2-(trans)-hydroxy-1,2,3,4-tetrahydro-1-naphthyloxy)-2-methyl-imidazo[1,2-a]pyridine, analogously to Example 9, produces the title compound of m.p. 138°–140° C.

16.
3-formyl-8-(2-(trans)-hydroxy-1-benzo[b]cycloheptanyloxy)-2-methyl-imidazo[1,2-a]pyridine The title compound of 163°–165° C. is obtained by reaction of 3-formyl-8-hydroxy-2-methyl-imidazo[1,2-a]pyridine with benzosuberene oxide analogously to the method described in Example 1 and after recrystallization from diethyl ether.

17.
3-hydroxymethyl-8-(2-(trans)-hydroxy-1-benzo[b]cycloheptanyloxy)-2-methyl-imidazo[1,2-a]pyridine Analogously to Example 8 the title compound of m.p. 228°–230° C. is obtained by reduction of 3-formyl-8-(2-(trans)-hydroxy-1-benzo[b]cycloheptanyloxy)-2-methyl-imidazo[1,2-a]pyridine with sodium borohydride.

18.
3-formyl-8-(2-(trans)-hydroxy-2,3-dihydro-1-indenylamino)-2-methyl-imidazo[1,2-a]pyridine The title compound of m.p. 236°–238° C. is obtained by reaction of 8-amino-3-formyl-2-methyl-imidazo[1,2-a]pyridine with 1,2-indenoxide analogously to the method described in Example 1.

19.
3-hydroxymethyl-8-(2-(trans)-hydroxy-2,3-dihydro-1-indenylamino)-2-methyl-imidazo[1,2-a]pyridine Analogously to Example 8 the title compound of m.p. 198°–200° C. is obtained by reduction of 3-formyl-8-(2-(trans)-hydroxy-2,3-dihydro-1-indenylamino)-2-methyl-imidazo[1,2a]pyridine with sodium borohydride.

20.
3-amino-8-(2-(trans)-hydroxy-1,2,3,4-tetrahydro-1-naphthyloxy)-2-methyl-imidazo[1,2-]pyridine-hydrochloride To a solution of 2 g 8-(2-(trans)-hydroxy-1,2,3,4-tetrahydro-1-naphthyloxy)-2-methyl-3-nitroso-imidazo[1,2-a]pyridine in a mixture consisting of 20 ml methanol and 20 ml saturated methanolic hydrochloric acid at room temperature, 1 g of commercial Raney nickel is added in small portions while stirring vigorously at 0° C. After 2 hours the precipitate is filtered off, the filtrate is evaporated to dryness in vacuo and purified over silica gel. The title compound is obtained as a viscouse mass.

21.
3-formyl-8-(2-(trans)-hydroxy-2,3-dihydro-1-indenyloxy)-2-methyl-imidazo[1,2-a]pyridine 12 g (68 mmol) of 3-formyl-8-hydroxy-2-methyl-imidazo[1,2-a]pyridine, 18 g (136 mmol) of 1,2-indenoxide and 9,6 ml (68 mmol) of triethylamine are stirred in 95 ml methanol/water (4:1) for 14 hours at 40° C. The mixture is evaporated at 50° C. in the rotary evaporator, mixed with 200 ml icewater, rendered alkaline with sodium hydroxide solution (approximately pH 13), and the precipitate is filtered off. The filtrate is shaken out with dichloromethane and the organic phase made up to 250 ml with dichloromethane, combined with the precipitate, dried with magnesium sulfate and purified with active charcoal. 250 ml of toluene is added, dichloromethane is distilled off, the mixture is purified at the boiling point with bleaching earth (e.g. Tonsil®), evaporated to half its volume and allowed to crystallize in the refrigerator. The yield of the titel compound m.p. 200°–202° C. is 17.6 g (84%).

22.
3-formyl-8-(2-(trans)-hydroxy-2,3-dihydro-1-indenyloxy)-2-methyl-imidazo[1,2-a]pyridine A mixture of 4.4 g (25 mmol) 3-formyl-8-hydroxy-2-methyl-imidazo[1,2-a]pyridine, 10.7 g (50 mmol) (trans)-2-bromo-1-indanol and 13.8 g of potassium carbonate is stirred in 120 ml of methanol/water (4:1) for 16 hours at 40° C. The mixture is worked up analogously to Example 21 and the yield of the title compound m.p. 200°–202° C. (from methanol) is 4.8 g (62%).

23.
3-formyl-8-(2-(trans)-hydroxy-2,3-dihydro-1-indenyloxy)-2-methyl-imidazo[1,2-a]pyridine 39.7 ml of 10 N potassium hydroxide solution is added to 85.2 g (400 mmol) (trans)-2-bromo-1-indanol in 600 ml isopropyl alcohol dropwise at room temperature while stirring, and the mixture is stirred for a further 15 minutes at room temperature. The isopropyl alcohol is distilled off at 40° C./5–8 mbar, 350 ml methanol/water (4:1), 30.4 g potassium carbonate and 35.2 g (200 mmol) 3-formyl-8-hydroxy-2-methyl-imidazo[1,2-a]pyridine are added and the mixture is stirred for a further 10 hours at 40° C. and 8 hours at room temperature. The mixture is worked up analogously to Example 21 and the yield of the title compound m.p. 200°–202° C. is 47.2 g (76.5%).

24.
6-chloro-3-formyl-8-(2-(trans)-hydroxy-2,3-dihydro-1-indenyloxy)-2-methyl-imidazo[1,2-a]pyridine The title compound of m.p. 220°–222° C. is obtained by reacting 6-chloro-3-formyl-8-hydroxy-2-methyl-imidazo[1,2-a]pyridine with 1,2-indenoxide analogously to the method described in Example 21 and after recrystallization from methanol.

25.
6-chloro-3-hydroxymethyl-8-(2-(trans)-hydroxy-2,3-dihydro-1-indenyloxy)-2-methyl-imidazo[1,2-a]pyridine Analogously to Example 8 the title compound of m.p. 210° C. (decomposition) is obtained by reducing 6-chloro-3-formyl-8-(2-(trans)-hydroxy-2,3-dihydro-1-indenyloxy)-2-methyl-imidazo[1,2-a]pyridine with sodium borohydride and recrystallization from methanol.

26.
6-chloro-8-(2-(trans)-hydroxy-2,3-dihydro-1-indenyloxy)-2-methyl-imidazo[1,2-a]pyridine The title compound of m.p. 175°–177° C. is obtained from 6-chloro-8-hydroxy-2-methyl-imidazo[1,2-a]pyridine reacting with 1,2-indenoxide analogously to the method described in Example 21 and after recrystallization from ethyl acetate.

27.
6-chloro-8-(2-(trans)-hydroxy-2,3-dihydro-1-indenyloxy)-2-methyl-3-nitroso-imidazo[1,2-a]pyridine Nitrosation of 6-chloro-8-(2-(trans)-hydroxy-2,3-dihydro-1-indenyloxy)-2-methyl-imidazo[1,2-a]pyridine analogously to Example 9 gives the title compound.

28.
3-amino-6-chloro-8-(2-(trans)-hydroxy-2,3-dihydro-1-indenyloxy)-2-methyl-imidazo[1,2-a]pyridine The title compound of m.p. 223°–225° C. is obtained. analogously to Example 10, by reducing 6-chloro-8-(2-(trans)-hydroxy-2,3-dihydro-1-indenyloxy)-2-methyl-3-nitroso-imidazo[1,2-a]pyridine with zinc in aqueous acetic acid and purification over silica gel (mobile phase mixture methylene chloride/methanol=95:5).

29.
8-(5-fluoro-2-(trans)-hydroxy-2,3-dihydro-1-indenyloxy)-3-formyl-2-methyl-imidazo[1,2-a]pyridine The title compound of m.p. 205° C. is obtained from 3-formyl-8-hydroxy-2-methyl-imidazo[1,2-a]pyridine in reaction with 5-fluoro-inden-1,2-oxide analogously to the method described in Example 22 and after recrystallization from methanol.

30.
8-(5-fluoro-2-(trans)-hydroxy-2,3-dihydro-1-indenyloxy)-3-hydroxymethyl-2-methyl-imidazo[1,2-a]pyridine Analogously to Example 8 the title compound of m.p. 197°–199° C. is obtained by reduction of 8-(5-fluoro-2-(trans)-hydroxy-2,3-dihydro-1-indenyloxy)-3-formyl-2-methyl-imidazo[1,2-a]pyridine with sodium borohydride and recrystallization from ethanol.

31.
8-(5-fluoro-2-(trans)-hydroxy-2,3-dihydro-1-indenyloxy)-2-methyl-imidazo[1,2-a]pyridine The title compound of m.p. 174°–175° C. is obtained by reaction of 8-hydroxy-2-methyl-imidazo[1,2-a]pyridine with 5-fluoro-inden-1,2-oxide analogously to the method described in Example 22 and after recrystallization from acetonitrile.

32.
8-(5-fluoro-2-(trans)-hydroxy-2,3-dihyro-1-indenyloxy)-2-methyl-3-nitroso-imidazo[1,2-a]pyridine Nitrosation of 8-(5-fluoro-2-(trans)-hydroxy-2,3-dihydro-1-indenyloxy)-2-methyl-imidazo[1,2-a]pyridine, analogously to Example 9, gives the title compound of m.p. 150° C. (with decomposition) after recrystallization from acetonitrile.

33.
3-amino-8-(5-fluoro-2-(trans)-hydroxy-2,3-dihydro-1-indenyloxy)-2-methyl-imidazo[1,2-a]pyridine-hydrochloride .

The title compound of m.p. 168°–170° C. is obtained analogously to Example 10 by reduction of 8-(5-fluoro-2-(trans)-hydroxy-2,3-dihydro-1-indenyloxy)-2-methyl-3-nitroso-imidazo[1,2-a]pyridine with zinc in aqueous acetic acid and precipitation of the hydrochloride from a 2-propanol solution with the aid of HCl/ether solution.

34.
(1'R,2'R)-3-formyl-8-(2-hydroxy-2,3-dihydro-1-indenyloxy)-2-methyl-imidazo[1,2-a]pyridine The title compound of m.p. 200°-202° C. is obtained as viscous oil by reaction of 3-formyl-8-hydroxy-2-methyl-imidazo[1,2-a]pyridine with (+)-(1S,2R)-indenoxide analogously to the method described in Example 21 and after purification over silica gel (mobile phase mixture methylene chloride/methanol=95:5). $[\alpha]_D^{22} = -122.2°$ (c=1, chloroform).

35.
(−)-(1'R,2'R)-3-hydroxymethyl-8-(2-hydroxy-2,3-dihydro-1-indenyloxy)-2-methyl-imidazo[1,2-a]pyridine Analogously to Example 8, the title compound of m.p. 198°-200° C. ($[\alpha]_D^{20} = -100°$, methylene chlorid/methanol=1/1) is obtained by reduction of (1'R,2'R)-3-formyl-8-(2-hydroxy-2,3-dihydro-1-indenyloxy)-2-methyl-imidazo[1,2-a]pyridine with sodium borohydride.

36.
(−)-(1'R,2'R)-3-cyanomethyl-8-(2-hydroxy-2,3-dihydro-1-indenyloxy)-2-methyl-imidazo[1,2-a]pyridine The title compound of m.p. 173°-174° C. ($[\alpha]_D^{20} = -219°$, chloroform) is obtained by reaction of 3-cyanomethyl-8-hydroxy-2-methyl-imidazo[1,2-a]pyridine with (+)-(1S,2R)-indenoxide analogously to the method described in Example 21 and after washing with cold methanol.

37.
(1'R,2'R)-8-(2-hydroxy-2,3-dihydro-1-indenyloxy)-2-methyl-imidazo[1,2-a]pyridine The title compound is obtained as an amorphous solid by reaction of 8-hydroxy-2-methyl-imidazo[1,2-a]pyridine with (+)-(1S,2R)-indenoxide analogously to the method described in Example 21 and after purification over silica gel (mobile phase mixture methylene chloride/methanol=95:5).

38.
(1'R,2'R)-8-(2-hydroxy-2,3-dihydro-1-indenyloxy)-2-methyl-3-nitroso-imidazo[1,2-a]pyridine Nitrosation of (1'R,2'R)-8-(2-hydroxy-2,3-dihydro-1-indenyloxy)-2-methyl-imidazo[1,2-a]pyridine, analogously to Example 9, gives the title compound after purification over silica gel (mobile phase mixture methylene chloride/methanol=95:5) as a green amorphous powder.

39.
(+)-(1'R,2'R)-3-amino-8-(2-hydroxy-2,3-dihydro-1-indenyloxy)-2-methyl-imidazo[1,2-a]pyridine-hydrochloride The title compound of m.p. 151°-152° C. ($[\alpha]_D^{20} = +31°$, methanol) is obtained, analogously to Example 10, by reducing (1'R,2'R)-8-(2-hydroxy-2,3-dihydro-1-indenyloxy)-2-methyl-3-nitroso-imidazo[1,2-a]pyridine with zinc in aqueous acetic acid and precipitating the hydrochloride from a 2-proponal solution with the help of HCl/ether solution.

40.
(+)-(1S,2S)-3-cyanomethyl-2-methyl-8-(2-hydroxy-2,3-dihydro-1-indenyloxy)-imidazo[1,2-a]pyridine 750 mg 3-cyanomethyl-8-hydroxy-2-methyl-imidazo[1,2-a]pyridine are reacted, analogously to the method described in Example 21, with 210 mg (−)-1R,2S-indenoxide and 400 mg triethylamine in aqueous methanol (60 ml methanol+15 ml water) at room temperature. After 3 days the solution is evaporated and the residue taken up in 50 ml water. The precipitate is filtered off and purified by chromatography over silica gel (mobile phase: ethyl acetate/methanol=10:1). After evaporation the residue is precipitated from methylene chloride/cyclohexane. 120 mg of the title compound is isolated. $[\alpha]_D^{22} = +113°$ (c=1, chloroform).

41.
(+)-(1S,2S)-3-formyl-2-methyl-8-(2-hydroxy-2,3-dihydro-1-indenyloxy)-imidazo[1,2-a]pyridine 3.30 g of 3-formyl-8-hydroxy-2-methyl-imidazo[1,2-a]pyridine and 1.40 g (−)-1R,2S-indenoxide are reacted, analogously to the method described in Example 21, with 1.90 g of triethylamine in 425 ml of aqueous methanol (350 ml methanol+75 g water) at 50° C. After 8 hours the solution is evaporated and the residue dissolved in 150 ml water. 4 g of sodium carbonate is added and extracted with 4×100 ml ethyl acetate. The organic phases are washed with 2×200 ml sodium carbonate solution and 4×200 ml water, dried over magnesium sulfate and evaporated. The solid residue is mixed in 100 ml cyclohexane filtered and dried. 1.51 g of the title compound in m.p. 187°-192° C. is isolated $[\alpha]_D^{22} = +112°$ (c=0.5, chloroform).

42.
(+)-(1S,2S)-3-hydroxymethyl-2-methyl-8-(2-hydroxy-2,3-dihydro-1-indenyloxy)-imidazo[1,2-a]pyridine A solution of 1.39 g (+)-(1S,2S)-3-formyl-2-methyl-imidazo[1,2-a]pyridine in 300 ml methanol is mixed with 350 mg sodium borohydride at 0° C. The mixture is warmed to room temperature, stirred for one hour and then mixed with 100 ml water. The methanol is evaporated on the rotary evaporator. After addition of 150 ml water, the solution is cooled to +4° C. and the precipitate obtained filtered off by suction. The moist residue is dissolved in 300 ml acetone, filtered and washed with diisopropyl ether. After drying in high vacuum, 960 mg of the title compound of m.p. 188°-192° C. is isolated. $[\alpha]_D^{22} = +105°$ (c=0.5, chloroform/methanol=1:1).

43.
(+)-(1S,2S)-3-formyl-2-methyl-8-(2-hydroxy-1,2,3,4-tetrahydro-1-naphthyloxy)-imidazo[1,2-a]pyridine 580 mg of 3-formyl-8-hydroxy-2-methyl-imidazo[1,2-a]pyridine and 580 mg of (+)-1R,2S-1,2,3,4-tetrahydro-naphthaline-1,2-oxide are reacted, analogously to the method described in Example 21, with 340 mg triethylamine in 43 ml of aqueous methanol (35 ml methanol+8 ml water) at 60° C. After 8 hours the mixture is worked up as described in Example 41. After stirring with petroleum ether and drying in high vacuum, 250 mg of the title compound is isolated. $[\alpha]_D^{22} = +38°$ (c=1, chloroform).

44.

(+)-(1S,2S)-3-hydroxymethyl-2-methyl-8-(2-hydroxy-1,2,3,4-tetrahydro-1-naphthyloxy-imidazo[1,2-a]pyridine A solution of 200 mg (+)-(1S,2S)-3-formyl-2-methyl-8-(2-hydroxy-1,2,3,4-tetrahydro-1-naphthyloxy)-imidazo[1,2-a]-pyridine in 75 ml of methanol is reacted, as described in Example 8, with 80 mg of sodium borohydride for 4 hours at room temperature. 100 ml of water is added and the methanol distilled off on the rotary evaporator. The precipitate in an aqueous residue is filtered off, washed with water and dried in high vacuum. 170 mg of the title compound of m.p. 102°-104° C. is isolated. $[\alpha]_D^{22} = +90°$ (c=0.5, chloroform).

45.

3-formyl-8-(2-(cis)-hydroxy-2,3-dihydro-1-indenyloxy)-2-methyl-imidazo[1,2-a]pyridine 1 g of 3-formyl-2-methyl-8-(2-(trans)-methylsulfonyloxy-2,3-dihydro-1-indenyloxy)-imidazo[1,2-a]pyridine is added to a mixture of 5.1 g of anhydrous potassium acetate, 13.8 g of 1,4,7,10,13,16-hexaoxacyclooctadecan ("18-crown-6) and 100 ml of anhydrous acetonitrile, while stirring and excluding any moisture. The brownish suspension is warmed for 18 hours at 70° C. and heated for a further 10 hours under reflux. After cooling, it is poured onto water and extraction carried out several times with dichloromethane. The organic phases are washed with water, dried and the solvent stripped off in vacuo. The dark brown residue is assayed by chromotography with the mobile phase ethyl acetate/methanol=95:5 (V/V) over silica gel. After stripping off of the solvent, the residue (0.18 g) is dissolved in 3.6 ml methanol and this solution is added dropwise with stirring to a solution of 0.072 g potassium hydroxide in 1.2 ml water. Stirring continues for one hour at room temperature, water is added, the pH is adjusted with diluted acetic acid to 6 and extraction is carried out several times with dichloromethane. The organic phases are washed with water, dried and the solvent is stripped off in vacuo. 115 mg of the title compound as a yellowish residue of m.p. 171°-173° C. is obtained.

46.

8-(2-(cis)-hydroxy-2,3-dihydro-1-indenyloxy)-3-hydroxymethyl-2-methyl-imidazo[1,2-a]pyridine A solution of 380 mg 3-formyl-3-(2-(cis)-hydroxy-2,3-dihydro-1-indenyloxy)-2-methyl-imidazo-[1,2-a]pyridine in 12 ml methanol is added dropwise to a solution of 80 mg sodium borohydride in 3 ml methanol. The solution is stirred for 1 hour at room temperature and for 8 hours at 50° C., allowed to cool and poured over icewater. The mixture is acidified with diluted acetic acid and extracted several times with dichloromethane. The combined extracts are dried, the solvent is distilled off and the brownish residue is assayed by chromotography with the mobile phase chloroform/methanol=10:1 (V/V) over silica gel. After evaporation and washing with diethyl ether the yield of the title compound of m.p. 174°-175° C. is 90 mg.

Starting Compounds

A. 8-amino-2-methyl-imidazo[1,2-a]pyridine-hydrobromide

A solution of 16.5 g 2-methyl-8-nitro-imidazo[1,2-a]pyridine-hydrobromide in 800 ml methanol is saturated with hydrogen at room temperature at low pressure for 8 hours after addition of a catalytic amount of commercial Pd/C-catalyst. The catalyst is then filtered off and the filtrate evaporated until dry. After recrystallization from acetonitrile 11.9 g of the title compound of m.p. 237°-238° C. is obtained.

B. 8-amino-2,3-dimethyl-imidazo[1,2-a]pyridine

Analogously to Example A 11.3 g of the title compound of m.p. 148°-150° C. is obtained by catalytic reduction of 19.0 g of 2,3-dimethyl-8-nitro-imidazo[1,2-a]pyridine dissolved in 700 ml methanol.

C. 2-methyl-8-nitro-imidazo[1,2-a]pyridine 20.0 g of 2-amino-3-nitropyridine and 22 g of bromoacetone are boild in 1 l ethanol for 55 hours under reflux. The mixture is then cooled in an icebath, the crystalline hydrobromide filtered off under suction and washed with ethanol. After drying in a vacuum at 50° C. the yield of the title compound of m.p. 300° C. (decomposition) is 17.2 g.

D. 3-formyl-2-methyl-8-nitro-imidazo[1,2-a]pyridine 20 ml phosphoroxychloride is added dropwise within 5 minutes to a solution of 7.6 g 2-methyl-8-nitro-imidazo[1,2-a]pyridine in 100 ml dimethylformamide at 0° C. After stirring for 1 hour at 0° C. and for 2 hours at 70° C. the mixture is cooled again to 0° C. 10 ml phosphoroxychloride is added dropwise and the same procedure is carried out as before. When the reaction is finished the mixture is poured over 200 ml icewater, neutralized with saturated sodium hydrogen carbonate solution and extracted 3× with 50 ml ethyl acetate each time. The solvent is stripped off in vacuo and the residue is washed with ether and recrystallized from acetonitrile, giving the title compound of m.p. 188°-189° C.

E. 8-amino-3-formyl-2-methyl-imidazo[1,2-a]pyridine 0.5 g 3-formyl-2-methyl-8-nitro-imidazo[1,2-a]pyridine, dissolved in 200 ml methanol, is hydrogenated after addition of a catalytic amount& of a commercial Pd/C-catalyst at room temperature at low pressure for 1½ hours.

The catalyst is then filtered off, the filtrate is evaporated to dryness in vacuo and the resultant crystalline residue is recrystallized from acetonitrile. The title compound of m.p. 146°-147° C. is obtained.

F. 6,8-dichloro-2-methyl-imidazo [1,2-a]pyridine

A mixture of 30 g 2-amino-3,5-dichloropyridine and 39 ml chloroacetone dissolved in 260 ml ethanol is heated under reflux for 64 hours. The volatile components are stripped off in vacuum and the residue suspended in 200 ml water. This is brought to pH 7-8 by means of saturated aqueous NaHCO$_3$-solution. A filtrate is obtained under suction and dried to constant weight in vacuo and recrystallized from cyclohexane. 17.8 g of the title compound of m.p. 156°-158° C. is obtained.

G.
8-benzyloxy-6-chloro-2-methyl-imidazo[1,2-a]pyridinehydrochloride 1.8 g commercial 80% sodium hydride in paraffin is added in small portions at room temperature to 5.4 ml benzyl alcohol dissolved in 300 ml dry dimethylformamide. The benzylate solution is stirred for a further 2 hours. Thereafter it is cooled to $-40°$ C., mixed with 10.0 g 6,8-dichloro-2-methyl-imidazo[1,2-a]pyridine and stirred for a further 4 hours. The temperature is allowed to rise gradually to 12° C. and the mixture is stirred at this temperature for 48 hours. Thereafter the solution is poured onto 1.5 kg icewater, the solution brought to pH=7 with 1 N-HCl and extracted 3× with 100 ml ethyl acetate each time. The combined extracts are dried with sodium sulfate and evaporated to dryness on the rotary evaporator. After dissolution in 100 ml 2-propanol, the title compound is precipitated by addition of saturated HCl-ether solution. After the precipitate has been filtered off under suction, it is recrystallized twice from isopropanol. 4.5 g of the title compound of m.p. 180°–182° C. being obtained.

H.
8-benzyloxy-6-chloro-3-formyl.2-methyl-imidazo[1,2-a]pyridine-hydrochloride The title compound of m.p. 137°–138° C. (from acetonitrile) is obtained, analogous y to Example D, from 8-benzyloxy-6-chloro-2-methyl-imidazo[1,2-a]pyridine and phosphoroxychloride/dimethylformamide.

I.
6-chloro-3-formyl-8-hydroxy-2-methyl-imidazo[1,2-a]pyridine

A mixture of 0.5 g 8-benzyloxy-6-chloro-3-formyl-2-methyl-imidazo[1,2-a]pyridine, 2.5 ml acetic acid and 2.5 ml 48% aqueous hydrogen bromide solution is heated under reflux for 2 hours. The mixture is cooled to room temperature, poured over 50 ml icewater, neutralized with 1 N-sodium hydroxide solution and extracted 3× with 20 ml ethyl acetate each time. The combined extracts are dried over sodium sulfate, the solvent is stripped off and the solid residue is recrystallized from dioxane. 0.2 g of the title compound of m.p. 256° C. (decomposition) is obtained.

J. 6-chloro-8-hydroxy-2-methyl-imidazo[1,2-a]pyridine

The title compound of m.p. 232° C. (decomposition) is obtained, analogously to Example I, by treating 8-benzyloxy-6-chloro-2-methyl-imidazo[1,2-a]pyridine with acetic acid/hydrogen bromide solution after purification over silica gel (mobile phase mixture ethyl acetate/petroleum ether=6:4).

K.
3-formyl-2-methyl-8-(2-(trans)-methylsulfonyloxy-2,3-dihydro-1-indenyloxy)-imidazo[1,2-a]pyridine 8.5 ml triethylamine is added, while stirring and excluding any moisture, to 10 g 3-formyl-8-(2-(trans)-hydroxy-2,3-dihydro-1-indenyloxy)-2-methyl-imidazo[1,2-a]pyridine, suspended in 200 ml dry dichloromethane. This is cooled in an icebath and 5 ml methane sulfonyl chloride dissolved in 10 ml dry dichloromethane is added dropwise. This is stirred for 1 hour while cooling with ice, and the solution is poured onto icewater and extracted several times with dichloromethane. The organic phases are washed with water and dried, and the solvent is stripped off in vacuo. The yellowish residue is stirred with diethyl ether, filtered off under suction and dried. 12 g of the title compound of m.p. 158°–160° C. is obtained. By analogous methods 2-methyl-8-(2-(trans)methylsulfonyloxy-2,3-dihydro-1-indenyloxy)-imidazo[1,2-a]pyridine is obtained from 2-methyl-8-(2-(trans)-hydroxy-2,3-dihydro-1-indenyloxy)-imidazo[1,2-a]pyridine and methane sulfonyl chloride. M.p. 122°–125° C. (decomposition).

Industrial Applicability

The compounds of formula I and their salts have valuable pharmacological properties which make them industrially useful. They have, in particular, an excellent protective effect on the stomach and intestine in warm-blooded animals. In addition, the compounds according to the invention are distinguished by a high degree of selectivity, the absence of significant side effects and a high therapeutic index.

In this context, "protective effect on the stomach and intestine" is understood as meaning the prevention and treatment of gastrointestinal diseases, in particular gastrointestinal inflammatory diseases and lesions (such as, for example, gastric ulcer, duodenal ulcer, gastritis, irritable stomach due to hyperacidity or medication), which may be caused, for example by microorganisms, bacteriotoxins, drugs (for example certain antiinflammatory agents and antirheumatics), chemicals (for example ethanol), gastric acid or stress situations.

In various models, in which the antiulcerogenic and the antisecretory properties were determined, the compounds according to the invention proved to be markedly superior in their excellent properties to the compounds known from the prior art.

On account of these properties, compounds of formula I and their pharmacologically tolerated salts are eminently suitable for use in human and veterinary medicine, where they are used in particular for the treatment and/or prophylaxis of ulcer conditions of the stomach and/or of the intestine.

The invention therefore also relates to the compounds according to the invention for use in the treatment and/or prophylaxis of the above-mentioned diseases.

The invention furthermore relates to the use of the compounds according to the invention for the preparation of drugs which are used for the treatment and/or prophylaxis of the above-mentioned diseases.

The invention also relates to the use of the compounds according to the invention for the treatment and/or prophylaxis of the above-mentioned diseases.

The invention furthermore relates to drugs which contain one or more compounds of formula I and/or their pharmacologically tolerated salts.

The drugs are prepared by methods which are known per se and familiar to one skilled in the art. As drugs, the pharmacologically active components (=active compounds) according to the invention are used either as such or, preferably, in combination with suitable pharmaceutical excipients or carriers, in the form of tablets, coated tablets, capsules, suppositories, plasters (for example as TTS), emulsions, suspensions or solutions, the content of active compound advantageously being between 0.1 and 95%.

The excipients and carriers which are suitable for the desired drug formulations are familiar to one skilled in the art from his technical knowledge. In addition to solvents, gel formers, suppository bases, tablet excipients and other carriers for active compounds, it is possible to use, for example, antioxidants, dispersants, emulsifiers, antifoams, flavour improvers, preservatives, solubilizers, colorants or, in particular, permeation promoters and complex formers (for example cyclodextrins).

The active compounds can be administered orally, parenterally or percutaneously.

In general, it has proved advantageous in human medicine, in the case of oral administration, to administer the active compound or compounds in a daily dose of about 0.01 to about 20, preferably 0.05 to 5, in particular 0.1 to 1.5, mg/kg body weight, if appropriate in the form <f several, preferably 1 to 4, individual doses in order to achieve the desired result. In the case of parenteral treatment, similar or (particularly in the case of intravenous administration of the active compounds) as a rule lower dosages can be used. The particular optimum dosage required and mode of administration of the active compounds can readily be established by anyone skilled in the art on the basis of his technical knowledge.

If the compounds and/or salts according to the invention are used for the treatment of the above-mentioned diseases, the pharmaceutical formulations can also contain one or more pharmacologically active constituents of other drug groups, such as antacids, for example aluminium hydroxide or magnesium aluminate; tranquillizers, such as benzodiazepines, for example diazepam; spasmolytics, such as, for example, bietamiverine or camylofine; anticholinergics, such as, for example, oxyphencyclimine or phencarbamide; local anaesthetics, such as, for example, tetracaine or procaine; antibacterials, such as, for example, penicillins or tetracyclines; and, if appropriate, also ferments, vitamins or amino acids.

In this case, the combination of the compounds according to the invention with drugs which inhibit acid secretion, such as, for example $H_2$ blockers (for example cimetidine or ranitidine), or with so-called peripheral anticholinergics (for example pirenzepine, telenzepine or zolenzepine), with the aim of reinforcing the principal action in an additive or superadditive sense and/or eliminating or reducing the side effects, or furthermore with antibacterial substances (for example cephalosporins, tetracyclines, nalidixic acid or penicillins) for the control of campylobacter pyloridis should be particularly singled out.

Pharmacology

The excellent gastric protective action and the gastric secretion-inhibiting action of the compounds according to the invention can be demonstrated in investigations on animal models. The compounds according to the invention which are investigated in the Table given below have been provided with numbers of the Examples.

Testing of the Antiulcerogenic and Secretion-Inhibiting Action on the Modified Shay Rat Table 1 below shows the effect of the compounds according to the invention after intraduodenal (i.d.) administration on lesion formation and acid secretion in the modified Shay rat.

TABLE 1

| Serial No. | N (number of animals) | Dose (μmol/kg) i.d. | Protective action on stomach | | Inhibition of acid secretion | |
|---|---|---|---|---|---|---|
| | | | Reduction in lesion index (%) | Approx. ED50*) (μmol/kg) i.d. | Reduction in HCl secretion (%) | Approx. ED50*) (μmol/kg) i.d. |
| 2 | 8 | 0.3 | 25 | 0.84 | −20 | 4.27 |
| | 16 | 1.0 | 47 | | 23 | |
| | 8 | 3.0 | 81 | | 52 | |
| | 8 | 10.0 | 94 | | 47 | |
| | 8 | 30.0 | 100 | | 95 | |
| 4 | 7 | 0.3 | 18 | 1.04 | −26 | 1.95 |
| | 8 | 0.6 | 33 | | 12 | |
| | 8 | 1.0 | 35 | | 22 | |
| | 8 | 1.5 | 94 | | 50 | |
| | 8 | 2.0 | 98 | | 51 | |
| | 8 | 3.0 | 93 | | 63 | |
| | 8 | 6.0 | 100 | | 73 | |
| | 8 | 30.0 | 100 | | 99 | |
| 8 | 7 | 0.1 | 13 | 0.69 | 10 | 12.9 |
| | 15 | 0.3 | 43 | | 19 | |
| | 16 | 1.0 | 47 | | 25 | |
| | 16 | 3.0 | 74 | | 20 | |
| | 16 | 10.0 | 94 | | 35 | |
| | 8 | 30.0 | 100 | | 98 | |
| 11 | 8 | 1.0 | 27 | 1.69 | 16 | 6.02 |
| | 8 | 3.0 | 71 | | 32 | |
| | 8 | 10.0 | 100 | | 67 | |
| 30 | 8 | 3.0 | 86 | | 41 | |

*) ED50 = dose (interpolated) which reduces the lesion index or the HCl secretion of the rat stomach in the treated group by 50% compared with the control group.

Method

Ulcers are provoked in rats which have fasted for 24 hours (female, 180–200 g, 4 animals per cage on high grid) by pylorus ligature (under diethyl ether anaesthesia) and oral administration of 100 mg/10 ml/kg acetylsalicylic acid. The substances to be tested are administered intraduodenally (2,5 ml/kg) immediately following t[e pylorus ligature. The wound is closed by means of Michel clamps. 4 hours later, the animals are sacrificed under ether anaesthesia by atlas dislocation and the stomach is resected.

The stomach is opened along the greater curvature and clamped on a cork sheet after first determining the amount of secreted gastric juice (volume) and subsequently its HCl content (titration with sodium hydroxide solution). Using a stereomicroscope at 10×magnification, the number and size (=diameter) of ulcers present are determined. The product of severity (according to the scale of points below) and number of ulcers serves as an individual lesion index.

| Scale of points: | |
|---|---|
| No ulcers | 0 |
| Ulcer diameter | |
| 0.1-1.4 mm | 1 |
| 1.5-2.4 mm | 2 |
| 2.5-3.4 mm | 3 |
| 3.5-4.4 mm | 4 |
| 4.5-5.4 mm | 5 |
| >5.5 mm | 6 |

The reduction in the mean lesion index of each treated group compared with the control group (=100%) serves as a measure of the antiulcerogenic effect. The ED50 designates the dose which reduces the mean lesion index or the HCl secretion by 50% compared with the control.

I claim:

1. A compound of formula I

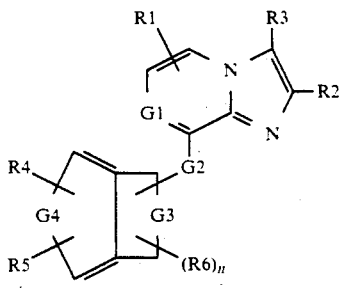

wherein

R1 denotes hydrogen (H) or halogen,

R2 denotes hydrogen (H), 1-4C-alkyl, hydroxy-1-4C-alkyl, halo-1-4C-alkyl, cyano-1-4alkyl or 1-4C-alkoxycarbonyl, R3 denotes hydrogen (H), 1-4C-alkyl, formyl, hydroxy-1-4C-alkyl, halo-1-4C-alkyl, cyano-1-4C-alkyl, amino-1-4C-alkyl, mono- or di-1-4C-alkylamino-1-4C-alkyl, nitroso, nitro, amino, mono- or di-1-4C-alkylamino or 1-4C-alkoxycarbonyl, R4 denotes hydrogen (H), 1-4C-alkyl, 1-4C-alkoxy, halogen or trifluoromethyl, R5 denotes hydrogen (H), 1-4C-alkyl, 1-4C-alkoxy, halogen or trifluoromethyl, R6 denotes hydrogen or 1-4C-alkyl, n denotes the numbers 1 or 2, G1 denotes CH or G2 denotes O (oxygen), NH, N-1-4C-alkyl or 1-4C-alkylene, G3 denotes 1-hydroxy-trimethylene —CH(OH)—CH$_2$—CH$_2$—), 2-hydroxy-3-methyl-trimethylene (—CH$_2$—CH(OH)—CH(CH$_3$)—), 2-hydroxy-trimethylene (—CH$_2$—CH(OH)—CH$_2$—), 1-hydroxy-tetramethylene (—CH(OH)—CH$_2$—CH$_2$—CH$_2$—), 2-hydroxy-tetramethylene (—CH$_2$—CH(OH)—CH$_2$—CH$_2$—), 1-hydroxy-pentamethylene (—CH(OH)—CH$_2$—CH$_2$—CH$_2$—CH$_2$—) or 2-hydroxy-pentamethylene (—CH$_2$—CH(OH)—CH$_2$—CH$_2$—CH$_2$—) and G4 denotes S (sulphur), O (oxygen) or vinylene (—CH=CH—), or a salt thereof.

2. A compound of formula I according to claim 1, wherein R1 denotes hydrogen (H) and G3 denotes 1-hydroxy-trimethylene (—CH(OH)—CH$_2$—CH$_2$—), 2-hydroxy-trimethylene (—CH$_2$—CH(OH)—CH$_2$—), 1-hydroxy-tetramethylene (—CH(OH)—CH$_2$—CH$_2$—CH$_2$—), 2-hydroxy-tetramethylene (—CH$_2$CH(OH)—CH$_2$—CH$_2$—)1-hydroxy-pentamethylene (—CH(OH)—CH$_2$—CH$_2$—CH$_2$—CH$_2$—) or 2-hydroxy-pentamethylene (—CH$_2$—CH(OH)—CH$_2$—CH$_2$—CH$_2$—) or a salt thereof.

3. A compound of formula I according to claim 1, wherein

R1 denotes hydrogen,

R2 denotes hydrogen, methyl, cyanomethyl or hydroxymethyl,

R3 denotes hydrogen, methyl, formyl, hydroxymethyl, chloromethyl, cyanomethyl or amino, R4 denotes hydrogen, methyl, chlorine or fluorine, R5 denotes hydrogen, R6 denotes hydrogen, G1 denotes CH, G2 denotes O (oxygen), NH or methylene, G3 denotes 2-hydroxy-trimethylene (—CH$_2$—CH(OH)—CH$_2$—), 2-hydroxy-tetramethylene (—CH$_2$—CH(OH)—CH$_2$—CH$_2$—) or 2-hydroxy-pentamethylene (—CH$_2$—CH(OH)—CH$_2$—CH$_2$—CH$_2$—), and G4 denotes O (oxygen), S (sulphur) or vinylene (—CH=CH—) or a salt thereof.

4. A compound of formula I according to claim 1, wherein

R1 denotes hydrogen,

R2 denotes methyl,

R3 denotes hydrogen, methyl, hydroxymethyl, cyanomethyl or amino,

R4 denotes hydrogen,

R5 denotes hydrogen,

R6 denotes hydrogen,

G1 denotes CH,

G2 denotes O (oxygen) or NH,

G3 denotes 2-hydroxy-trimethylene (—CH$_2$—CH(OH)—CH$_2$—), or 2-hydroxy-tetramethylene (—CH$_2$—CH(OH)—CH$_2$—CH$_2$—) and G4 denotes vinylene (—CH=CH—) or a salt thereof.

5. A compound of formula I according to claim 1, wherein

R1 denotes hydrogen, chlorine or fluorine,

R2 denotes hydrogen, methyl, ethyl, hydroxymethyl, chloromethyl, cyanomethyl, methoxycarbonyl or ethoxycarbonyl, R3 denotes hydrogen, methyl, formyl, hydroxymethyl, chloromethyl, cyanomethyl, dimethylaminomethyl, amino, dimethylamino, methoxycarbonyl or ethoxycarbonyl, R4 denotes hydrogen, methyl, methoxy, chlorine, fluorine or trifluoromethyl, R5 denotes hydrogen, methyl, methoxy, chlorine or fluorine, R6 denotes hydrogen or methyl, n denotes the numbers 1 or 2, G1 denotes CH or G2 denotes O (oxygen), NH or methylene, G3 denotes 1-hydroxy-trimethylene (—CH(OH)—CH$_2$—CH$_2$—), 2-hydroxy-3-methyl-trimethylene (—CH$_2$—CH(OH)—CH(—CH$_3$)—), 2-hydroxy-trimethylene (—CH$_2$—CH(OH- )—CH₂—), 1-hydroxy-tetramethylene (—CH(OH)—CH₂—CH₂—CH₂—), 2-hydroxy-tetramethylene (—CH₂—CH(OH)—CH₂—CH₂—) or 1-hydroxy-pentamethylene (—CH(OH)—CH₂—CH₂—CH₂—CH₂—) or 2-hydroxy-pentamethylene (—CH₂—CH(OH)—CH₂—CH₂—CH₂—) and G4 denotes O (oxygen) S (sulphur) or vinylene, or a salt thereof.

6. A compound according to claim 1, characterized by formula I*

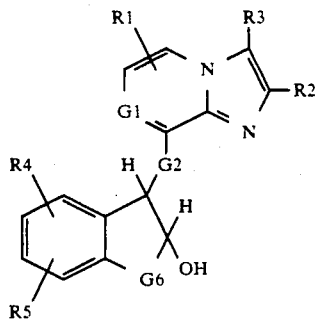

wherein

R1 denotes hydrogen, chlorine or fluorine.

R2 denotes hydrogen, methyl, ethyl or hydroxymethyl,

R3 denotes hydrogen, methyl, formyl, hydroxymethyl, cyanomethyl or amino,

R4 denotes hydrogen, methyl, ethyl methoxy, ethoxy, chlorine, fluorine or trifluoromethyl.

R5 denotes hydrogen, methyl, ethyl chlorine or fluorine,

G1 denotes CH,

G2 denotes O (oxygen) or NH and

G6 denotes —CH₂—, —CH(CH₃)—, —CH₂CH₂— or —CH₂CH₂CH₂—, or a salt thereof.

7. A compound of formula I* according to claim 6, wherein

R1 denotes hydrogen,

R2 denotes methyl,

R3 denotes hydrogen, methyl, hydroxymethyl, cyanomethyl or amino,

R4 denotes hydrogen or fluorine,

R5 denotes hydrogen,

G1 denotes CH,

G2 denotes O (oxygen) or NH and

G6 denotes —CH₂— or —CH₂CH₂—, or a salt thereof.

8. A compound of formula I*,

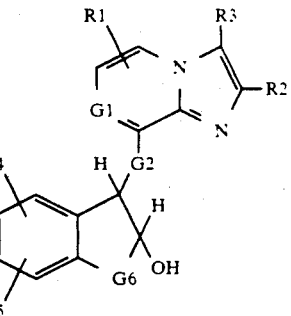

wherein

R1 denotes hydrogen or halogen,

R2 denotes 1–4C-alkyl,

R3 denotes hydrogen, 1–4C-alkyl, formyl, hydroxymethyl, cyanomethyl or amino,

R4 denotes hydrogen or halogen,

R5 denotes hydrogen,

G1 denotes CH,

G2 denotes O (oxygen) or NH.

G6 denotes —CH₂—, —CH₂CH₂— or —CH₂CH₂CH₂—, or a salt thereof.

9. The compound of claim 1 which is 2-ethyl-3-hydroxymethyl-8-(2-hydroxy-2,3-dihydro-1-indenyloxy)-imidazo[1,2-a]pyridine or a salt thereof.

10. A drug composition containing suitable excipient or carrier and an effective amount of a compound according to claim 1 or a pharmacologically tolerated salt thereof.

11. A process for prophylaxis or treatment of gastrointestinal disease which comprises administering to a human or other warm-blooded animal, subject to or afflicted with gastrointestinal disease, an effective amount of a compound according to claim 1, or a pharmacologically-tolerated salt thereof.

* * * * *

UNITED STATES PATENT AND TRADEMARK OFFICE
CERTIFICATE OF CORRECTION

PATENT NO. : 5,112,834
DATED : May 12, 1992
INVENTOR(S) : Senn-Bilfinger

Page 1 of 2

It is certified that error appears in the above-identified patent and that said Letters Patent is hereby corrected as shown below:

Title page, right column, the formula in the Abstract; column 1, lines 28 to 40; and claim 1, column 25, lines 26 to 37; each of the designated formulae should read:

--

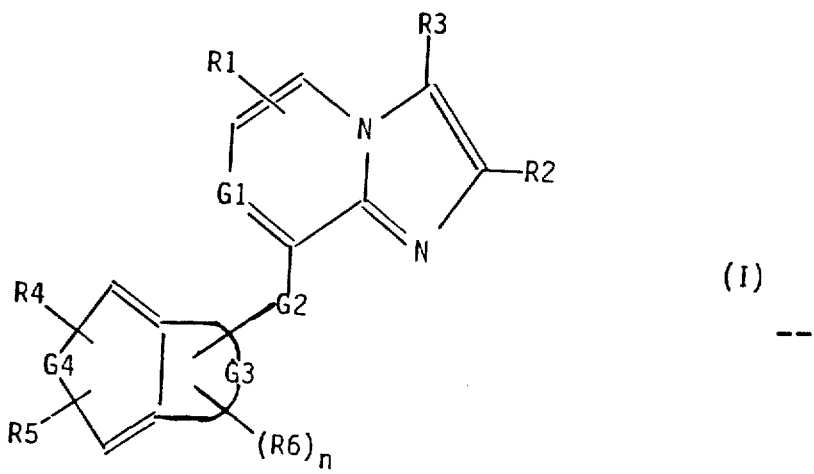

(I)

--

UNITED STATES PATENT AND TRADEMARK OFFICE
CERTIFICATE OF CORRECTION

PATENT NO. : 5,112,834

DATED : May 12, 1992

INVENTOR(S) : Senn-Bilfinger

It is certified that error appears in the above-identified patent and that said Letters Patent is hereby corrected as shown below:

```
Column 25, line 59,  "-CH(OH-" should read --(-CH(OH- --;
Column 26, line 9,   "1-hydroxy" should read --, 1-hydroxy--;
           line 11,  "CH₂-)" should read --CH₂- --;
           line 31,  "or" should read --, or--;
           line 46,  "or" should read --, or--;
           line 63,  "CH or" should read --CH,--.
Column 27, line 8,   "S" should read --, S--;
           line 33,  "ethyl" should read --ethyl,--;
           line 35,  "ethyl" should read --ethyl,--.
Column 28, line 7,   "formula 1*," should read --forumla 1*--.
```

Signed and Sealed this

Fourteenth Day of September, 1993

Attest:

BRUCE LEHMAN

*Attesting Officer*  Commissioner of Patents and Trademarks